United States Patent
Conway

(10) Patent No.: US 10,201,434 B2
(45) Date of Patent: Feb. 12, 2019

(54) GARMENT HAVING INTEGRATED PROSTHETIC BREASTS

(71) Applicant: Kathleen Bona Conway, Wilmette, IL (US)

(72) Inventor: Kathleen Bona Conway, Wilmette, IL (US)

( * ) Notice: Subject to any disclaimer, the term of this patent is extended or adjusted under 35 U.S.C. 154(b) by 23 days.

(21) Appl. No.: 15/491,174

(22) Filed: Apr. 19, 2017

(65) Prior Publication Data

US 2017/0296359 A1   Oct. 19, 2017

Related U.S. Application Data

(60) Provisional application No. 62/324,851, filed on Apr. 19, 2016.

(51) Int. Cl.
| | |
|---|---|
| *A41C 3/08* | (2006.01) |
| *A61F 2/52* | (2006.01) |
| *A41B 9/06* | (2006.01) |
| *A41D 1/22* | (2018.01) |
| *A41D 7/00* | (2006.01) |

(52) U.S. Cl.
CPC ............ *A61F 2/52* (2013.01); *A41B 9/06* (2013.01); *A41C 3/08* (2013.01); *A41D 1/22* (2013.01); *A41D 7/00* (2013.01); *A61F 2002/523* (2013.01)

(58) Field of Classification Search
CPC .... A41C 3/00; A41C 3/08; A41C 3/12; A41C 3/007; A41C 3/148; A41C 3/0057
USPC ............ 450/36, 39, 54–57; 2/267, 268
See application file for complete search history.

(56) References Cited

U.S. PATENT DOCUMENTS

| | | | | |
|---|---|---|---|---|
| 3,401,407 A | * | 9/1968 | Pittman | A61F 2/52 450/57 |
| 3,714,107 A | * | 1/1973 | Smith | D21H 19/385 428/330 |
| 3,795,921 A | * | 3/1974 | Zucker | A61F 2/52 450/55 |
| 4,637,398 A | * | 1/1987 | Sherwood | A41C 3/148 450/54 |
| 4,854,915 A | * | 8/1989 | Luedy | A41C 3/148 450/31 |
| 5,478,278 A | * | 12/1995 | Greenblatt | A41C 3/0057 2/67 |
| 5,492,501 A | * | 2/1996 | Brown | A41C 3/12 2/73 |
| 5,938,394 A | * | 8/1999 | Christenson | B65F 3/001 220/1.5 |
| 6,811,462 B1 | * | 11/2004 | Kenneally | A41C 3/08 2/67 |

(Continued)

*Primary Examiner* — Gloria Hale
(74) *Attorney, Agent, or Firm* — Law Office of Marc D. Machtinger, Ltd.

(57) ABSTRACT

A garment having integrated prosthetic breasts is disclosed. The garment includes an inner front layer, a middle component which includes at least one, and ideally two prosthetic breast members. The prosthetics are lightweight so that no elastic across the torso is needed. An outer front layer covers the middle component. The middle component is formed of a mesh layer which is sewn to the inner front layer only at the neckline and arms, and has an open bottom edge. The prosthetic breast members are attached to the mesh layer and provide shaping for mastectomy patients or other individuals having a need or desire for natural looking shaping.

18 Claims, 3 Drawing Sheets

(56) References Cited

U.S. PATENT DOCUMENTS

| | | | | |
|---|---|---|---|---|
| 7,086,925 B2* | 8/2006 | Kaye | ............... | A41C 3/12 |
| | | | | 2/267 |
| 2003/0181129 A1* | 9/2003 | Getman | ............... | A41C 3/0057 |
| | | | | 450/57 |
| 2006/0057936 A1* | 3/2006 | Knox | ............... | A41C 3/0007 |
| | | | | 450/57 |
| 2008/0026676 A1* | 1/2008 | Rothman | ............... | A41C 3/08 |
| | | | | 450/36 |
| 2013/0205463 A1* | 8/2013 | Leung | ............... | A41D 1/215 |
| | | | | 2/48 |

* cited by examiner

GARMENT HAVING INTEGRATED PROSTHETIC BREASTS

CROSS-REFERENCES

This application claims the benefit of U.S. Provisional Patent Application No. 62/324,851 filed on Apr. 19, 2016, which is hereby incorporated by reference in its entirety.

BACKGROUND OF THE INVENTION

Field of the Invention

The present invention relates to garments having integrated prosthetic breasts, and more particularly, to a garment having prosthetic breasts which can be comfortably worn by double mastectomy patients and is suitably worn as an outer layer.

Background

It is known that bilateral mastectomy survivors have a psychological need for at least a temporary replacement of the breasts. Prosthetic breasts have been provided and used in the past and various garments of wearing apparel have been provided to accommodate the wearing of these items. Such garments are generally provided with pockets to receive the prosthetic breast or breasts so that the wearer, when wearing the garment, will appear to the casual observer to be unaffected by the surgical process.

Such garments are important to the mental well-being of the patient after undergoing such a traumatic operation. One such garment commonly used for this purpose is a pocketed bra, with artificial breast or prosthesis-receiving pockets. Unfortunately, because of the scarring left from bilateral mastectomy surgery as well as scarring from removal of lymph nodes, wearing a bra can be quite uncomfortable for the survivor. Mastectomy scars across the chest along the bra band and extending under the arms can be quite sensitive and painful for the survivor.

Additionally, many bilateral mastectomy survivors also have had a lymphadenectomy (removal of lymph nodes), which can impede the flow of lymphatic fluid, putting the survivor at high risk for lymphedema. Lymphedema can occur spontaneously, resulting in swelling in the chest and/or arms, and which is not curable. Wearing a pocketed bra that is tight or restrictive at the bra band is not only uncomfortable atop the surgical scars, but it also puts the survivor at greater risk for lymphedema.

Another garment commonly used for this purpose is a pocketed camisole. Camisole-like garments are designed with artificial breast or prosthesis-receiving pockets constructed on the inside of the garment by use of a built-in shelf bra. Again, because of the bilateral mastectomy scar running along the chest and extending under the arms, as well as the scarred area left by the lymphadenectomy, the built-in shelf bra can be very uncomfortable and at times painful.

Furthermore, prosthetics that are to be worn in the pockets of the bra or camisole are quite heavy, some weighing as much as one pound each. Wearing heavy prosthetics can be uncomfortable for the mastectomy survivor as the extra weight on the bra straps cause the straps to be tight and restrictive, putting the survivor at higher risk for lymphedema. Also, the heavy prosthetics can lead to neck and shoulder pain because of the weight.

Such conventional garments are often fabricated to resemble undergarments or similar wearing apparel. These garments are not suitable for use as outer layers of clothing.

While various garments having pockets for prosthetic breasts have been proposed, there remains a need for a garment which provides at least one prosthetic breast which produces a natural look and alleviates the above problems, among other features and advantages.

SUMMARY

The present invention is a garment having prosthetic breast members. The garment may be suitable for use as underwear or as an outer layer of clothing.

The garment includes an inner front layer which lies on the chest of the wearer. Preferably, this layer is a soft and comfortable material. Ideally, there are no pockets, seams, or elastic on this layer which would contact or irritate the individual wearing the garment.

A middle component or layer is provided on the outer side of the inner front layer. The middle component is preferably a mesh lining which is sewn to the inner layer. Ideally, the sewn edges are along the neckline and arms only, and a bottom edge is left open so that no seams are disposed on the inner layer which would contact the individual. This enables the wearer to have a soft flat piece of fabric along the chest and under the arms, without causing irritation along the bilateral mastectomy or lymphadenectomy scars. There is also no tightness or restricting bra band that could heighten the risk for lymphedema.

Prosthetic breast members are attached to the mesh lining. These include either one or two prosthetics, as needed. The prosthetics include at least a back layer formed of any suitable material, and a shaped front layer, preferably formed of a molded foam bra cup. The layers may be sewn or fused together, leaving a small gap for filling, and then fully closed once filled. An optional additional layer may be used for rigidity, such as interfacing, however, it is not necessary in all embodiments. Optionally, the back layer may be a foam layer which holds its shape.

Preferably, the prosthetics are extremely light weight so as to provide a natural look without the need for elastic or tight straps. To achieve this light weight, a very lightweight filling is preferably used. For example, various conventional lightweight microbeads may be used. The garment is ideally suited for double mastectomy patients having a need for two prosthetic breasts. Conventional products are intended to meet the needs of a range of individuals, including individuals who have survived a single mastectomy procedure. Such individuals have an existing breast, and thus, conventional garments with prosthetics typically include a supporting strap for the existing natural breast. However, due to the scarring which typically extends across the chest in bilateral mastectomy patients, such garments having elastic or restrictive straps that extend across the chest are uncomfortable and problematic, as referenced above. Thus, the garment according to the present invention, which is ideally free of elastic or constricting straps, and preferably free of seams in the chest and torso region, provides a greatly needed solution for double mastectomy patients, as well as providing a solution for other individuals having a desire or need for a garment with two prosthetic breasts. Furthermore, in situations where two prosthetics are used, as there is no need to match the size and shape of an existing natural breast, permanently configured lightweight prosthetics can be used.

An outer front layer is provided over the middle component and provides a natural look without seams over the portion which covers the prosthetics. In certain embodiments, this garment may be worn as outerwear as there is no stitching to resemble underwear. It may be sleeveless, sleeved, it may be a bathing suit, or alternatively, it may be worn as underwear.

Still other objects and advantages of the present invention will become readily apparent to those skilled in the art from the following detailed description, wherein it is shown and described only the preferred embodiments of the invention, simply by way of illustration of the best mode contemplated of carrying out the invention. As will be realized, the invention is capable of other and different embodiments and its several details are capable of modifications in various obvious respects, without departing from the invention. Accordingly, the drawings, wherein like reference numerals represent like features, and description are to be regarded as illustrative in nature and not as restrictive.

DETAILED DESCRIPTION OF THE INVENTION

Figure 1:
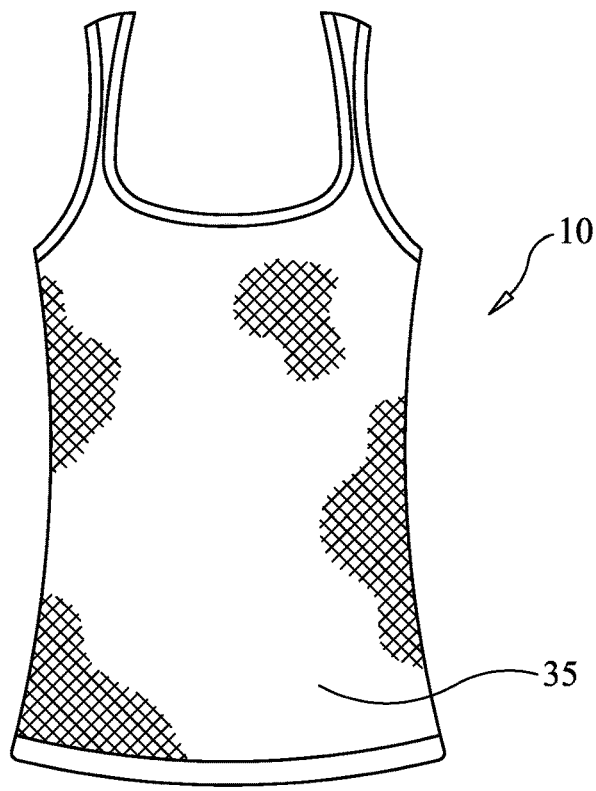
FIG. 1 illustrates a front view of a garment in accordance with one embodiment of the present invention.
Figure 2:
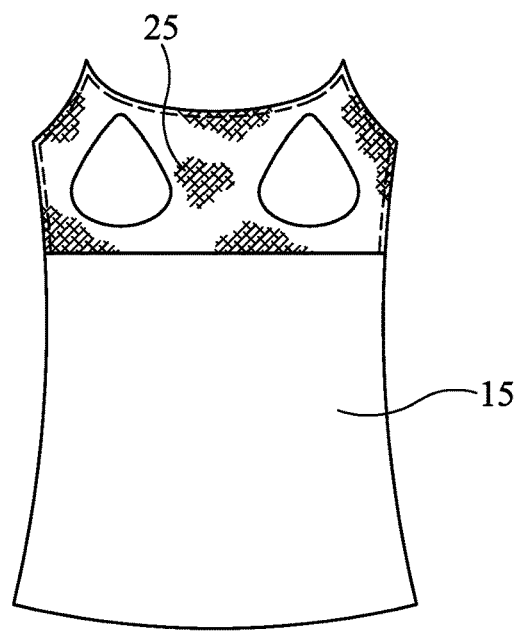
FIG. 2 illustrates a front view of a garment with the outer front layer removed, in accordance with one embodiment of the present invention.
Figure 3:
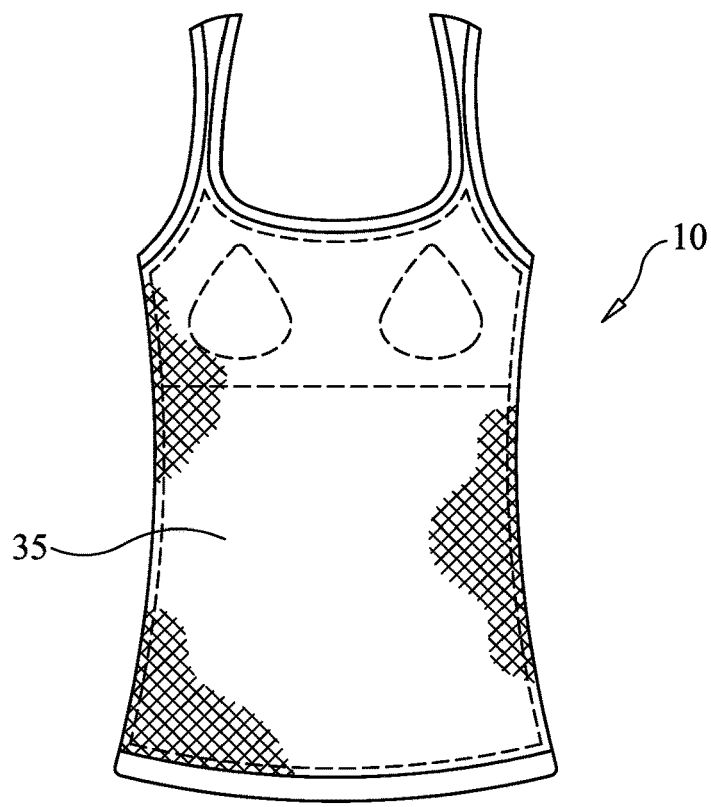
FIG. 3 illustrates a front view of a garment showing multiple layers in accordance with one embodiment of the present invention.
Figure 4:
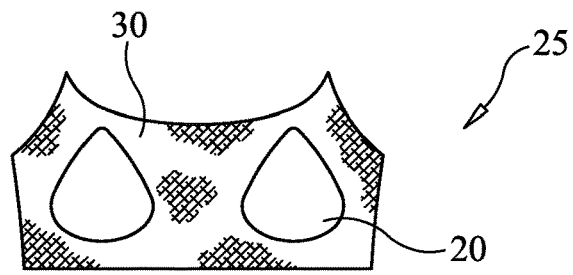
FIG. 4 illustrates a front view of the middle component of a garment in accordance with one embodiment of the present invention.
Figure 5:
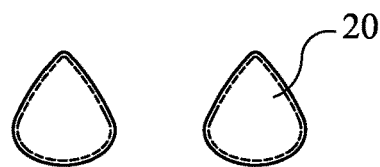
FIG. 5 illustrates a front view of the prosthetic breast members in accordance with one embodiment of the present invention.
Figure 6:
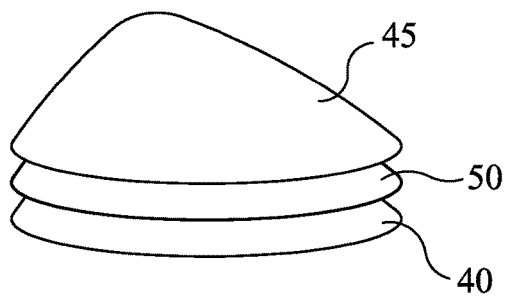
FIG. 6 illustrates a perspective view of the prosthetic breast members in accordance with one embodiment of the present invention.
Figure 7:
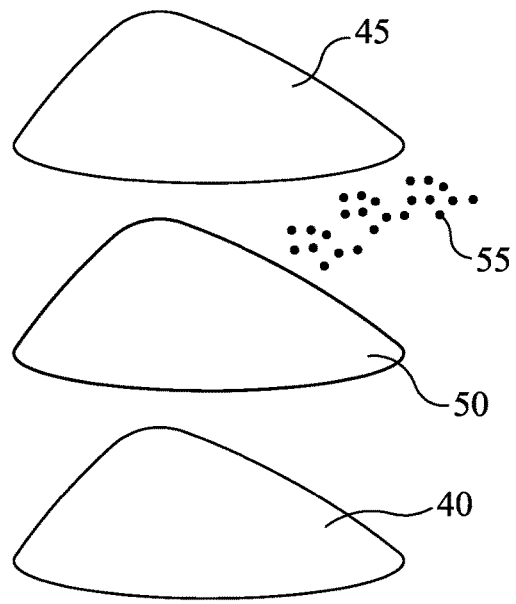
FIG. 7 illustrates a perspective view of the prosthetic breast members in accordance with one embodiment of the present invention.
Figure 8:
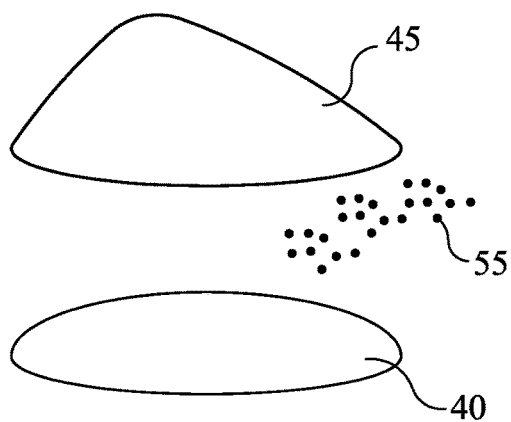
FIG. 8 illustrates a perspective view of the prosthetic breast members in accordance with one embodiment of the present invention.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

In various embodiments, the present invention is garment 10 having at least one integrated prosthetic breast 20, and preferably two prosthetic breasts 20.

In various embodiments, the garment 10 includes an inner front layer 15. The inner front layer 15 is preferably a soft an comfortable material which contacts the skin without any irritating seams or elastic. A middle component 25 is attached to the inner front layer 15. The middle component 25 includes a backing 30. The backing 30 may be a mesh material, or any suitable material.

The middle component 25 also includes either one or two prosthetic breast members 20 attached to the backing 30. The backing 30 is preferably sewn to the inner front layer 15 only at the top and sides, such as at the neckline and arms. Thus, the bottom edge is preferably left free so that no seam is formed in the portion of the inner front layer 15 which lies behind the prosthetic breast members 20.

In various embodiments, an outer front layer 35 is sewn to the inner front layer 15. The outer front layer 35 ideally covers the prosthetic breast members 20 without showing any seams. Thus, the garment 10 may be suitably designed as a sleeveless garment, a sleeved garment, a top only, a dress, a bathing suit, or even be worn as an undergarment. Optionally, the garment may include adjustable or stretchable straps.

The prosthetic breast members 20 of the garment 10 may be formed in any suitable manner. Preferably, they are lightweight, permanent, non-removable prosthetics integral with the garment 10. While the garment 10 can be formed having a single prosthetic breast member 20, the garment 10 is best suited for the unique needs of double mastectomy patients, or individuals having a need or desire to utilize two prosthetic breast members 20.

In certain embodiments, the prosthetic breast members 20 include a back layer 40, and a shaped front layer 45. The front layer 45 is preferably a molded foam bra cup. The back layer 40 may be a material layer, and an optional interfacing or middle layer 50 may be included to provide structure. Alternatively, the back layer 40 may be a foam layer which holds its shape, and middle layer 50 may be omitted.

In various embodiments, there is a lightweight filling 55 between back layer 40 and front layer 45. Any suitable lightweight filling which provides a natural look is contemplated. One preferred filling 55 is a lightweight microbead filling, commercially available. Ideally, each prosthetic is lightweight, weighing no more than 8.0 ounces each, but preferably weighing less than 5.0 ounces each, or even lighter, so as to eliminate problematic weight burdens and provide a natural look without the need for elastic or constricting bra straps. Ideally, there is no elastic material across the chest area of the garment 10, although the garment 10 optionally includes shoulder straps which may include elastic material.

While specific embodiments have been illustrated and described, numerous modifications come to mind without significantly departing from the spirit of the invention and the scope of protection is limited by the scope of the accompanying claims.

What is claimed is:

1. A garment having integrated prosthetic breasts comprising:
    an inner front layer forming an inner side of said garment adapted to be worn over a wearer's chest,
    a middle component comprising at least one prosthetic breast member,
    an outer front layer covering said middle component forming an outer side of said garment adapted to be worn over a wearer's chest,
    wherein said middle component comprises a backing layer and said at least one prosthetic breast member is attached to said backing layer, and wherein said backing layer is sewn to a portion of said inner front layer and unattached at an open lower edge.

2. The garment according to claim 1, wherein the portion of said inner front layer is adjacent a neck line.

3. The garment according to claim 1, wherein the portion of said inner front layer is adjacent a neck line and sleeve lines.

4. The garment according to claim 1, wherein said at least one prosthetic breast member comprises a back layer, and shaped front layer attached to said back layer, and a filling, wherein said shaped front layer protrudes outward toward a center region to replicate the shape of a woman's breast, and wherein said at least one prosthetic breast member comprises two prosthetic breast members.

5. The garment according to claim 4, wherein said filling comprises microbeads.

6. The garment according to claim 5, wherein said shaped front layer comprises a molded foam bra cup.

7. The garment according to claim 6, wherein said back layer is comprised of foam.

8. The garment according to claim 7, wherein said shaped front layer is fused or sewn to said back layer.

9. The garment according to claim 3, wherein said inner front layer is devoid of seams at a portion which lies behind and encompasses an entire area of said at least one prosthetic breast member.

10. The garment according to claim 9, wherein said outer front layer conceals any seams at an outer portion which lies in front of and encompasses the entire area of said at least one prosthetic breast member.

11. The garment according to claim 10, wherein said inner front layer, said middle component, and said outer front layer are devoid of elastic material across a chest area of the garment.

12. The garment according to claim 10, wherein said at least one prosthetic breast member weighs less than 8.0 ounces.

13. The garment according to claim 10, wherein said at least one prosthetic breast member is not selectively removable.

14. The garment according to claim 10, wherein said garment is a sleeveless garment.

15. The garment according to claim 10, wherein said garment is a sleeved garment.

16. The garment according to claim 10, wherein said garment is an outerwear garment.

17. The garment according to claim 10, wherein said garment is a bathing suit.

18. The garment according to claim 10, wherein said garment is an underwear garment.

* * * * *